United States Patent [19]

Friedhofen et al.

[11] 4,371,691

[45] Feb. 1, 1983

[54] PREPARATION OF POLYCARBONATE FROM SPECIFIC CRUDE BISPHENOLS

[75] Inventors: Gerhard Friedhofen; Volker Serini; Rainer Neumann; Dieter Freitag; Hans-Helmut Schwarz, all of Krefeld, Fed. Rep. of Germany

[73] Assignee: Bayer Aktiengesellschaft, Leverkusen, Fed. Rep. of Germany

[21] Appl. No.: 167,269

[22] Filed: Jul. 9, 1980

[30] Foreign Application Priority Data

Jul. 13, 1979 [DE] Fed. Rep. of Germany ....... 2928464

[51] Int. Cl.$^3$ ........................................... C08G 63/62
[52] U.S. Cl. .................................. 528/196; 528/198; 528/204
[58] Field of Search ....................... 528/196, 198, 204

[56] References Cited

U.S. PATENT DOCUMENTS

| | | | |
|---|---|---|---|
| 2,191,831 | 2/1940 | Perkins | 568/722 |
| 2,845,464 | 7/1958 | Luten | 568/722 |
| 3,049,568 | 8/1962 | Apel et al. | 568/722 |
| 3,073,868 | 1/1963 | Prahl et al. | 568/722 |
| 3,112,292 | 11/1963 | Bottenbruch et al. | 528/196 |
| 3,213,060 | 10/1965 | Jackson et al. | 528/196 |
| 3,219,549 | 11/1965 | Prahl et al. | 568/722 |
| 3,242,219 | 3/1966 | Farnham et al. | 568/722 |
| 3,267,075 | 8/1966 | Schnell et al. | 528/196 |
| 3,335,111 | 8/1967 | Pray et al. | 528/196 |
| 3,394,089 | 7/1968 | McNutt et al. | 568/722 |
| 3,410,823 | 11/1968 | Cleveland | 528/196 |
| 3,437,639 | 4/1969 | Beach et al. | 528/196 |
| 3,668,181 | 6/1972 | Oxenrider | 528/196 |
| 3,673,262 | 6/1972 | Prahl et al. | 568/722 |
| 3,936,507 | 2/1976 | Ligorati et al. | 568/722 |
| 4,169,211 | 9/1979 | Ligorati et al. | 568/722 |
| 4,212,774 | 7/1980 | Idel | 528/196 |

FOREIGN PATENT DOCUMENTS 1410750 10/1975 United Kingdom.
1521605 8/1978 United Kingdom.

OTHER PUBLICATIONS

Hackh's Chemical Dictionary, 4th Ed., pp. 27, 250, 548 & 117.

*Primary Examiner*—Harold D. Anderson
*Attorney, Agent, or Firm*—Gene Harsh; Lawrence S. Pope; Aron Preis

[57] ABSTRACT

This disclosure relates to the processes for producing polycarbonates from specific crude bisphenols. The bisphenols are characterized in that immediately after their preparation they are subjected to (i) separation, of excess phenols and low-boiling substances, by means of an evaporator, and (ii) removal of monophenols by desorption.

The invention also relates to high-molecular weight aromatic polycarbonates made of crude bisphenols and their use in a variety of applications.

6 Claims, No Drawings

PREPARATION OF POLYCARBONATE FROM SPECIFIC CRUDE BISPHENOLS

BACKGROUND OF THE INVENTION

It is known that bisphenols can be prepared by condensation of phenols with carbonyl compounds, biscarbinols, dienes or alkines by a large number of processes (in this context, see, for example, U.S. Pat. No. 2,191,831; U.S. Pat. No. 2,845,464; German Pat. No. 1,242,237; U.S. Pat. No. 3,073,868; U.S. Pat. No. 3,673,262; French Pat. No. 1,374,477; U.S. Pat. No. 3,394,089; and German Offenlegungsschrift No. 2,422,532). Where highly pure bisphenols are desired for use in the preparation of polycarbonates, special procedures for the process or subsequent expensive purification steps are required (in this context, see, for example, U.S. Pat. No. 3,049,568; German Pat. No. 1,186,874; German Pat. No. 1,168,445; Italian Pat. No. 650,774; German Offenlegungsschrift No. 2,359,500; German Offenlegungsschrift No. 2,364,164; and German Offenlegungsschrift No. 2,537,027.

The reason for these special procedures and for the expensive purification steps is that in general only highly pure bisphenols can be employed for the preparation of high-molecular thermoplastic polycarbonates (see, for example, German Pat. No. 1,186,874 or German Offenlegungsschrift No. 2,537,027.

Even according to German patent application No. P 28 11 182.2, which does not constitute a prior publication, a crystallization stage is a prerequisite to further use of the bisphenols for the preparation of polycarbonates, and in particular, a crystallization stage in the exchanger resin bed used for the preparation of the bisphenols.

It was thus surprising that high-molecular, thermoplastic polycarbonates of good quality are obtainable from crude bisphenols—preferably crude bisphenols possessing at least 2 alkyl substituents, and in particular, 4 alkyl substituents—by known processes for the preparation of polycarbonates, i.e., the phase boundary polycondensation process, without maintaining particular reaction conditions. The fact that the starting materials for the preparation of the polycarbonates, namely, the crude bisphenols, are obtainable in a particularly simple manner is regarded as a special advantage of the process.

SUMMARY OF THE INVENTION

The present invention relates to a process for the preparation of thermoplastic, aromatic, high-molecular polycarbonates from specific crude bisphenols by known methods, in particular by the phase boundary method, which is characterized in that bisphenols which have been prepared by known processes and, immediately after their preparation, have been separated off from excess phenols and low-boiling substances in an evaporator at temperatures between 100° and 300° C., and under pressures between 0.05 and 1,000 millibars, and from which the residual monophenols have subsequently been removed, down to a content of less than 5% by weight, of monophenols, relative to the residue, by means of desorption using inert gases.

The present invention also relates to the high-molecular aromatic polycarbonates obtainable by the process according to the invention and their use as shaped articles, coatings, fibers, lacquers and films, by themselves or in combination with other substances.

A DETAILED DESCRIPTION OF THE INVENTION

A simple possible method of preparing the crude bisphenols which can be employed in the practice of the invention entails, for example, a reaction of phenols with carbonyl compounds, dienes, alkines or biscarbinols, the molar ratio of phenols to other reactants being between 2:1 and 40:1, at temperatures below 120° C., preferably below 80° C., in the presence of acid catalysts, a separation of excess phenol and low-boiling substances in an evaporator at temperatures between 100° C. and 300° C., preferably at temperatures between 150° C. and 250° C., and under pressures between 0.05 and 1,000 millibars, preferably between 0.5 and 500 millibars, and then a reduction of the residual monophenols content to less than 5% by weight, preferably to less than 2.5% by weight, and in particular, to less than 0.5% by weight, relative to the bisphenol by means of desorption in an appropriate temperature and pressure ranges using an inert gas, preferably nitrogen.

In the context of the present invention, crude bisphenols are preferably those having 2 alkyl substituents, and in particular, 4 alkyl substituents, and which also contain minor amounts of other phenolic components.

The use of crude bisphenols according to the present invention has at least two advantages: first, it saves energy, since the crude bisphenols are bottom products; and second, the monophenols separated off can be fed back into the bisphenol preparation.

Phenols for the method mentioned above for the preparation of crude bisphenols are, for example, the phenols of the general formula

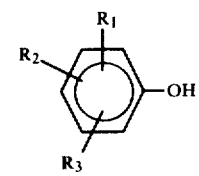

(1)

wherein $R_1$, $R_2$ and $R_3$ are identical or different and denote H, $CH_3$, $C_2H_5$ or $C_3H_7$.

Suitable phenols are, for example, phenol, cresols and 2,6-dialkylphenols, in particular 2,6-dimethylphenol.

Carbonyl compounds suitable for the above-mentioned preparation of crude bisphenols are those which are described in the literature for the preparation of bisphenols. Examples of such carbonyl compounds are the following compounds of the general formula (2)

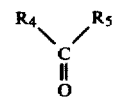

(2)

wherein $R_4$ and $R_5$ are identical or different and denote H or $C_nH_{2n+1}$,
in which
n=1 to 15,
or of the general formula (3)

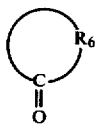

(3)

wherein $R_6$ is a divalent radical $-CH_2-(CH_2-)_m-CH_2-$
in which
$m = 3$ to 13.

Preferred carbonyl compounds are formaldehyde, acetone, butanone and cyclohexanone.

Dienes which are suitable for the above-mentioned simple possible method of preparing crude bisphenols are those which are described in the literature for the preparation of bisphenols. Examples of such dienes are alkyl- and dialkyl-butadienes, such as methyl- and dimethyl-butadiene.

Preferred dienes are butadiene, 2,3-dimethylbuta-1,3-diene and 2-methylbuta-1,3-diene.

Alkines which are suitable for the above-mentioned simple possible method of preparing crude bisphenols are those which are described in the literature for the preparation of bisphenols. Examples of such alkines are the following compounds of the general formula (4)

wherein $R_7$ and $R_8$ are identical or different and denote H or $C_nH_{2n+1}$,
in which
$n = 1$ to 5.

Preferred alkines are ethine, propine and butines.

Biscarbinols which are suitable for the above-mentioned simple possible method of preparing crude bisphenols are those which are described in the literature, such as, for example

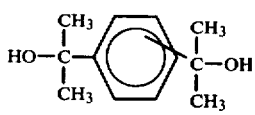

Preferred biscarbinols are 1,4-bis-2-(2-hydroxypropyl)-benzene and 1,3-bis-2-(2-hydroxypropyl)-benzenes.

Acid catalysts which are suitable for the above-mentioned simple possible method of preparing crude bisphenols are those which are described in the literature for the preparation of bisphenols. Examples of such acid catalysts are hydrochloric acid, sulphuric acid, phosphoric acids, sulphonic acids and acid organic ion exchangers.

Low-boiling substances in the context of the process according to the invention can be, for example, $H_2O$, carbonyl compounds, dienes, alkines, biscarbinols and acid catalysts.

Examples of evaporators which are suitable for the process according to the invention are falling film evaporators, falling stream evaporators, thin film evaporators, bubble evaporators and spiral evaporators. Further industrial embodiments are described in the technical literature (in this context, see "Ullmanns Encyclopädie der technischen Chemie" ("Ullmanns Encyclopedia of Industrial Chemistry"), 3rd edition, Verlag Urban and Schwarzenberg, Munich-Berlin, 1951, Volume 1).

Evaporation is preferably carried out continuously, however, discontinuous evaporation is also possible, during which the temperatures and the pressure can be kept constant as distillation conditions or varied continuously or stepwise in the bottom of the column.

In principle, any gas or vapor which is inert under the reaction conditions, for example, in addition to nitrogen, Ar, He, Ne, $CO_2$, CO, $H_2$, $H_2O$ vapor, methane or halogenated hydrocarbons, can be used for the desorption in the process according to the invention.

Examples of suitable equipment for the desorption stage of the process according to the invention are falling film evaporators, falling stream evaporators and thin film evaporators.

The preferred desorption embodiment is a column with trays or packing, such as is described in the above-mentioned literature.

The desorption stage can follow immediately after the evaporation stage for the phenols, or if appropriate, an intermediate tank can be inserted between the evaporation stage and the desorption stage, with or without a conveying unit. The desorption can be carried out under the same temperature and pressure ranges as that for the evaporation. However, neither the pressure nor the temperature have to match specifically; rather, different values can be chosen in each case for the temperature and pressure, within the possible ranges, in the evaporation stage and in the desorption stage.

The amount of inert gas to be employed in the desorption stage is between about 0.05 and 50 m³ per kg of phenols to be desorbed.

The desorption is usually carried out continuously, but a discontinuous procedure is also possible. The temperature and pressure can be kept constant in the discontinuous procedure. Continuous or stepwise alteration of the temperature and pressure and of the amount of inert gas is also possible.

Surprisingly, the crude bisphenols obtained can be used immediately, without purification, in particular without crystallization, extraction, adsorption, rectification, sublimation or distillation, for the preparation of high-molecular polycarbonates by known processes.

Examples of suitable crude bisphenols are those which contain at least 50% by weight, preferably 80% by weight and particularly preferably 90% by weight, of one of the following bisphenols: α,α'-bis-(4-hydroxyphenyl)-p-diisopropylbenzene, α,α'-bis-(4-hydroxy-3,5-dimethylphenyl)-p-diisopropylbenzene, 2,2-bis-(4-hydroxyphenyl)-propane, 1,1-bis-(4-hydroxyphenyl)-cyclohexane, 2,2-bis-(3-methyl-4-hydroxyphenyl)-propane, bis-(3,5-dimethyl-4-hydroxyphenyl)-methane, 2,2-bis-(3,5-dimethyl-4-hydroxyphenol)-propane, bis-(4-hydroxyphenyl)sulphide and bis-(4-hydroxyphenyl)sulphone.

The crude bisphenols have a purity of not more than 99% by weight, generally not more than 97% by weight and often less than 95% by weight. The impurities are generally especially phenolic compounds of unknown structure having more than one aromatic radical.

In addition to the crude bisphenols, pure bisphenols customarily used for the preparation of polycarbonates can also be used, in any desired amount, in the polycarbonate preparation process according to the invention; preferred bisphenols of this type are: bis-(4-hydroxyphenyl) sulphone, bis-(4-hydroxyphenyl) sulphide, 2,2-bis-(4-hydroxyphenyl)-propane, 1,1-bis-(4-hydroxyphenyl)-cyclohexane, 2,2-bis-(3-methyl-4-hydroxyphenyl)-propane, bis-(3,5-dimethyl-4-hydroxyphenyl)-methane, 2,2-bis-(3,5-dimethyl-4-hydroxyphenyl)-propane, 2,2-bis-(3,5-dichloro-4-hydroxyphenyl)-propane, 2,2-bis-(3,5-dibromo-4-hydroxyphenyl)-propane, α,α'-bis-(4-hydroxyphenyl)-p-diisopropylbenzene and α,α'-bis-(4-hydroxy-3,5-dimethylphenyl)-p-diisopropylbenzene.

2,2-bis-(4-hydroxyphenyl)-propane and 2,2-bis-(3,5-dimethyl-4-hydroxyphenyl)-propane are particularly preferred.

The preparation of thermoplastic, aromatic polycarbonates is known in principle. They can be synthesized, for example, by the melt transesterification process, from bisphenol and diphenyl carbonate, or by the solution process, from bisphenol and phosgene using pyrridine as an auxiliary base, or by the two-phase boundary process, also from bisphenol and phosgene, these processes are described, for example, in the monograph by H. Schnell, *Chemistry and Physics of Polycarbonates*, New York-London-Sydney, Interscience Publishers 1964, Polymer Reviews, Volume 9 and in German Offenlegungsschriften Nos. 2,063,050; 2,063,052; 1,570,703; 2,211,956; 2,211,957; 2,248,817; and 2,615,038.

In general, the crude bisphenols can be reacted by at least one of the above-mentioned processes to give high-molecular polycarbonates. Thus, for example, crude bisphenols containing predominantly 2,2-bis-(3,5-dimethyl-4-hydroxyphenyl)-propane can be reacted by the two-phase boundary process to give high-molecular polycarbonates (compare German Offenlegungsschrifts Nos. 2,063,050 and 2,063,052).

In the two-phase boundary process, crude bisphenols are dissolved in the aqueous phase as alkali metal salts and are reacted with phosgene in the presence of organic solvents for the polycarbonate formed, such as, for example, chlorinated aliphatics or aromatics, such as methylene chloride and chlorobenzene, or mixtures of such solvents. The aqueous phase is kept alkaline during the condensation reaction, usually by adding alkali. The catalysts used for the condensation reaction are, for example, tertiary aliphatic amines, such as triethylamine, tributylamine and N-ethylpiperidine, or onium compounds, especially quaternary alkylammonium compounds, such as tetrabutylammonium bromide, or mixtures of these compounds. Chain limiters, such as phenols, for example, phenol, cresol, dimethylphenol and p-tert.-butylphenol, are used in the customary manner to limit the chain length. It is also possible to obtain branched polycarbonates by adding polyfunctional compounds.

It has been found that the crude bisphenols are particularly advantageous when used according to the invention in the phase boundary process since they are particularly soluble in the alkaline-aqueous phase and since the tendency of the polycarbonates formed to gel in chlorinated solvents is exceptionally low.

The advantages for the melt transesterification process are the good fusibility of the crude bisphenols and the low tendency of the polycarbonates to crystallize. This is also generally quite significant for thermoplastic processing. The advantage for the process in a homogeneous phase system is the particularly good solubility of the crude bisphenols in organic solvents.

The polycarbonates obtainable by the process according to the invention have average molecular weights $\overline{M}_w$ of at least 20,000, preferably of at least 25,000. Average molecular weights ($\overline{M}_w$) of up to over 200,000 can be achieved. However, average molecular weights ($\overline{M}_w$) of below 100,000, in particular below 60,000, are in general preferred for use in the thermoplastic sector.

Surprisingly, the high-molecular, aromatic polycarbonates prepared from crude bisphenols by the process according to the invention essentially have the same good properties as the conventional polycarbonates from purified bisphenols. Moreover, there are even considerable improvements in a number of their properties. Thus, in general, they have an exceptionally good solubility in organic solvents, and in particular also in lacquer solvents and in polymerizable monomers, such as, for example, styrene, acrylonitrile, vinyl chloride, methyl methacrylate and mixtures thereof, which is advantageous for grafting reactions. They can thus be used as the base for the preparation of graft polymers.

They also exhibit improved rheological properties in the melt, that is to say, better flow properties and an improved intrinsic viscosity over that of conventional polycarbonates. The critical thickness is also improved, for example, in the case of polycarbonates consisting predominantly of 2,2-bis-(4-hydroxyphenyl)-propane. The cross-linking ability of films by, for example, electron beams, which is significant for various applications, is also improved. Furthermore, in many cases, flame-proofing is facilitated since smaller amounts of flame-proofing agents (such as, for example, co-condensed 2,2-bis-(3,5-dibromo-4-hydroxyphenyl)-propane) are required for the same degree of flame retardance. The tracking resistance is also frequently significantly increased.

It is particularly surprising that the known compatibility of polycarbonates with other polymers is retained, since it is known that even small changes in the polymers frequently cause significant changes in the compatibility and hence in the properties. Thus, for example, compared with polycarbonates based on the corresponding pure bisphenol, there is virtually no difference in the compatibility of polycarbonates based on crude bisphenols containing predominantly 2,2-bis-(3,5-dimethyl-4-hydroxyphenyl)-propane with polyvinyl chloride (compare German Offenlegungsschrift No. 2,402,176), with polycarbonates based on 2,2-bis-(4-hydroxyphenyl)-propane (compare German Offenlegungsschrift No. 2,248,818) and with styrene polymers (compare German Offenlegungsschrift No. 2,329,585 and German Offenlegungsschrift No. 2,329,646). As a result, outstanding polymer blends are also obtained with the polycarbonates according to the invention.

It is also of significance that the polycarbonates retain their hydrolytic stability, especially the polycarbonates based on crude bisphenols containing predominantly 2,2-bis-(3,5-dimethyl-4-hydroxyphenyl)-propane (compare German Offenlegungsschrift No. 2,063,050 and German Offenlegungsschrift No. 2,211,957).

The polycarbonates according to the invention can very easily be processed to shaped articles, coatings, fibers, lacquers and films. Certain blends with other polymers, such as, for example, polyvinyl chloride, styrene polymers and polycarbonates obtained from purified bisphenols, can also advantageously be used. It is also possible to successfully use the polycarbonates according to the invention and polymer blends thereof in mixtures with fillers (such as, for example, minerals, wood flour and carbon black) reinforcing substances (such as, for example, glass fibers, asbestos and carbon fibers), substances which produce special effects, dyestuffs, pigments, stabilizers (for example, heat, oxidation and UV stabilizers) lubricants and mold release agents, flameproofing additives (such as, for example, halogenated aromatic compounds, metal oxides and metal salts) and other additives. They are particularly advantageous in cases where good electrical properties, a high heat distortion resistance, good toughness properties and a high stability towards saponification are required. They can thus be used, for example, for high-grade electrical components, electrical insulating films, pipelines for alkaline and acid liquors, housings, components for the automobile sector and for domestic appliances.

EXAMPLE 1

Preparation of tetramethylbisphenol A is carried out continuously in a fixed bed reactor. The reaction tube is 1,000 mm long and has a diameter of 100 mm. It is thermostatically controlled at 65° C. by jacket heating. It is filled with 6 liters of an anhydrous H+ ion exchanger. 600 ml of reaction solution/hour are pumped through this tube. On entry into the reactor, the reaction solution has the following composition: 97.6% by weight of dimethylphenol, 2.3% by weight of acetone and 0.1% by weight of β-mercaptopropionic acid.

At the reactor outlet, the reaction solution has the following composition: 89.6% by weight of dimethylphenol, 0.4% by weight of acetone, 0.5% by weight of $H_2O$, 9.1% by weight of tetramethylbisphenol A, 0.1% by weight of β-mercaptopropionic acid and 0.2% by weight of unknown components. The reaction solution is continuously passed, at a temperature of 190° C. and under 27 mbar, through a spiral evaporator which is heated with oil and has a tube length of 3.5 m and a tube diameter of 10 mm. 2,6-dimethylphenol is condensed via a cyclone provided with a short packed column, and in a condenser, which is operated at 50° C. The 2,2-bis-(3,5-dimethyl-4-hydroxyphenyl)-propane, which still contains 1.5% of 2,6-dimethylphenol, flows out of the spiral evaporator into a thin film evaporator equipped with a rotor, as the functioning desorber. The desorber is heated to 185° C. with oil and is operated under the same pressure as the spiral evaporator. A stream of nitrogen is passed at a rate of 6 liters/hour into the bottom of the desorber.

The crude bisphenol (180 g/hour) is collected in a receiver. It contains less than 0.1% of 2,6-dimethylphenol, 4.9% of unknown components and 95% of bis-(3,5-dimethyl-4-hydroxyphenyl)-propane. The color number of the crude bisphenol is 600 (hazen color number).

A polycarbonate with excellent properties can be prepared from this crude bisphenol (see Example 2).

EXAMPLE 2

Preparation of a polycarbonate from the crude bisphenol of Example 1.

568.8 g of the crude bisphenol from Example 1 and 5.6 g of phenol were dissolved in 2,286 ml of distilled water and 614.4 ml of 45% strength sodium hydroxide solution. After adding 1,490 ml of methylene chloride, 448 ml of chlorobenzene, 7.72 g of tetrabutylammonium bromide and 5.70 ml of tri-n-butylamine to the solution, 336.4 g of gaseous phosgene were passed into the mixture in the course of 60 minutes, while stirring. After the passing of 250 g of phosgene, an additional 96 ml of 45% strength sodium hydroxide solution were added. After adding 5.6 ml of triethylamine, the mixture was stirred for 30 minutes. The organic phase was then worked up by acidifying with dilute $H_3PO_4$, diluting with methylene chloride and washing with $H_2O$ until free from electrolytes. The polycarbonate obtainable by evaporating off the organic solvent had a relative viscosity ($\eta_{rel}$) of 1.296 (measured as in Example 4) and displayed outstanding properties.

EXAMPLE 3

Bisphenol A was prepared in a manner analogous to that in Example 1, except that 2,6-dimethylphenol was replaced by phenol. The crude bisphenol contained 0.1% of phenol, 8.3% of at least 7 unknown components and 91.6% of bisphenol A.

A polycarbonate with excellent properties can be prepared from this crude bisphenol (see Example 4).

EXAMPLE 4

Preparation of a polycarbonate from the crude bisphenol of Example 3.

204 ml of 45% strength sodium hydroxide solution were dissolved in 1,347 ml of distilled water, and 228 g of the crude bisphenol of Example 3 were added. When the crude bisphenol had almost dissolved, 1,381 ml of methylene chloride were added. Phosgene was passed in, while stirring vigorously, until the batch was free from bisphenolate. During the introduction of phosgene, the pH was kept at 13–14 by adding 45% strength sodium hydroxide solution. The temperature was kept between 20° and 30° C. The phosgene was introduced over a period of 15 minutes and then 0.75 ml of triethylamine was added and the mixture was stirred for a further 30 minutes at 25° C. The organic phase was worked up by acidifying with dilute phosphoric acid and then washed with water until freed from electrolytes. The polycarbonate obtained after evaporating the methylene chloride had a relative viscosity ($\eta_{rel}$) of 1.312 (measured on 0.5 g of polycarbonate in 100 ml of $CH_2Cl_2$ solution at 25° C.) and displayed outstanding properties.

What is claimed is:

1. In the process for the preparation of a thermoplastic, aromatic, high-molecular weight polycarbonate from at least one crude bisphenol, the improvement comprising:
   (i) separating said at least one crude bisphenol, immediately after its preparation, from excess of at least one phenol and low boiling substance, in an evaporator at a temperature between 100° and 300° C., and under a pressure of between 0.05 and 1000 millibars, and
   (ii) subjecting said crude bisphenol to desorption using an inert gas to attain a presence therein of monophenols of less than 2.5 percent by weight.

2. The process according to claim 1 wherein said temperature is between 150° and 250° C.

3. The process according to claim 1 wherein said pressure is between 0.5 and 500 millibars.

4. The process according to claim 1 wherein said at least one crude bisphenol has at least 2 alkyl substituents.

5. The process according to claim 1 wherein said at least one crude bisphenol has at least 4 alkyl substituents.

6. The process in accordance with claim 1 wherein said presence of monophenols is less than 0.5 percent by weight.

* * * * *